(12) United States Patent
Gillies et al.

(10) Patent No.: US 9,978,145 B2
(45) Date of Patent: May 22, 2018

(54) ASSESSMENT OF AN ATTENTIONAL DEFICIT

(71) Applicant: KONINKLIJKE PHILIPS N.V., Eindhoven (NL)

(72) Inventors: Murray Fulton Gillies, Eindhoven (NL); Laura Klaming, Utrecht (NL); Daisy Van Minde, Eindhoven (NL)

(73) Assignee: Koninklijke Philips N.V., Eindhoven (NL)

( * ) Notice: Subject to any disclaimer, the term of this patent is extended or adjusted under 35 U.S.C. 154(b) by 0 days. days.

(21) Appl. No.: 14/962,602

(22) Filed: Dec. 8, 2015

(65) Prior Publication Data

US 2016/0171696 A1     Jun. 16, 2016

(30) Foreign Application Priority Data

Dec. 16, 2014     (EP) .................................... 14198284

(51) Int. Cl.
*G06T 7/00*     (2017.01)
*A61B 5/00*     (2006.01)
(Continued)

(52) U.S. Cl.
CPC .......... *G06T 7/0016* (2013.01); *A61B 5/0077* (2013.01); *A61B 5/11* (2013.01);
(Continued)

(58) Field of Classification Search
CPC ....... A61B 3/032; A61B 3/0091; A61B 3/113; A61B 5/168; A61B 5/0077; A61B 5/11;
(Continued)

(56) References Cited

U.S. PATENT DOCUMENTS

| 8,668,337 B2 | 3/2014 | Waldorf et al. | |
| 2007/0200927 A1* | 8/2007 | Krenik | A61B 3/032 348/47 |

(Continued)

FOREIGN PATENT DOCUMENTS

| EP | 2131266 A2 | 9/2009 |
| JP | 2011212430 A | 10/2011 |

(Continued)

OTHER PUBLICATIONS

Anderson et al, "Exploiting Human Sensitivity to Gase for Tracking the Eyes", Behavior Research Methods, vol. 32, Issue 3, Sep. 2011, pp. 843-852.

(Continued)

*Primary Examiner* — Neil Mikeska

(57) ABSTRACT

A system and method are provided for use in the assessment of an attentional deficit. During the assessment, a test image is presented to a subject on a display. A camera image is obtained from a camera which is indicative of a geometric relation between the head of the subject and the display during the assessment. The camera image is analyzed to determine a deviation in the geometric relation between the head of the subject and the display from a reference geometric relation. Deviation data is then generated and output which is indicative of the deviation. Advantageous uses of the deviation data include providing visual feedback to the user, adjusting the test image, and taking the deviation into account when processing test data of the assessment. Advantageously, the need for a trained professional to be present during the assessment is reduced or avoided.

17 Claims, 7 Drawing Sheets

(51) Int. Cl.

| | |
|---|---|
| *A61B 5/16* | (2006.01) |
| *G06K 9/00* | (2006.01) |
| *G06K 9/52* | (2006.01) |
| *G06T 7/60* | (2017.01) |
| *A61B 5/11* | (2006.01) |
| *G06F 3/01* | (2006.01) |
| *G06F 19/00* | (2018.01) |
| *A61B 3/113* | (2006.01) |

(52) U.S. Cl.
CPC .............. *A61B 5/168* (2013.01); *G06F 3/012* (2013.01); *G06F 19/363* (2013.01); *G06K 9/0061* (2013.01); *G06K 9/00255* (2013.01); *G06K 9/00268* (2013.01); *G06K 9/00288* (2013.01); *G06K 9/52* (2013.01); *G06T 7/60* (2013.01); *A61B 3/113* (2013.01); *G06T 2207/30041* (2013.01); *G06T 2207/30201* (2013.01)

(58) Field of Classification Search
CPC ... H04N 7/15; H04L 65/1083; H04L 65/4053; H04L 65/403; H04L 65/1096; G06T 7/0016; G06T 7/60; G06K 9/52; G06K 9/00268; G06K 9/0061; G06K 9/00288; G06F 3/01; G06F 19/363
See application file for complete search history.

(56) References Cited

U.S. PATENT DOCUMENTS

| | | | | |
|---|---|---|---|---|
| 2008/0027352 | A1* | 1/2008 | Chiba | A61B 5/16 600/558 |
| 2008/0297589 | A1* | 12/2008 | Kurtz | H04N 7/147 348/14.16 |
| 2009/0118593 | A1* | 5/2009 | Jung | G06Q 50/22 600/300 |
| 2010/0016730 | A1 | 1/2010 | Tanaka et al. | |
| 2010/0085363 | A1* | 4/2010 | Smith | G06T 13/40 345/473 |
| 2011/0085017 | A1* | 4/2011 | Robinson | H04L 12/1827 348/14.08 |
| 2012/0101346 | A1* | 4/2012 | Scott | A61B 5/1124 600/300 |
| 2012/0274736 | A1* | 11/2012 | Robinson | H04N 7/15 348/14.16 |
| 2012/0308972 | A1 | 12/2012 | Miller et al. | |
| 2013/0090562 | A1 | 4/2013 | Ryan | |
| 2013/0110009 | A1* | 5/2013 | Salorio | A61M 21/00 600/595 |
| 2013/0278899 | A1* | 10/2013 | Waldorf | A61B 3/032 351/209 |
| 2014/0046193 | A1 | 2/2014 | Stack | |
| 2014/0139655 | A1* | 5/2014 | Mimar | G08B 21/0476 348/77 |
| 2014/0240313 | A1* | 8/2014 | Varga | G06T 19/006 345/419 |
| 2014/0309806 | A1* | 10/2014 | Ricci | B60Q 1/00 701/1 |
| 2014/0313488 | A1* | 10/2014 | Kiderman | A61B 3/145 351/246 |

FOREIGN PATENT DOCUMENTS

| | | |
|---|---|---|
| WO | 2010042730 A1 | 4/2010 |
| WO | 2013091132 A1 | 6/2013 |
| WO | 2013159841 A1 | 10/2013 |

OTHER PUBLICATIONS

Nakatani et al, "Horizontal Visual Search in a Learge Field by Patients With Unilateral Spatial Neglect", Journal of Clinical Neuroscience, vol. 20, No. 6, 2013, 1 Page Abstract.

\* cited by examiner

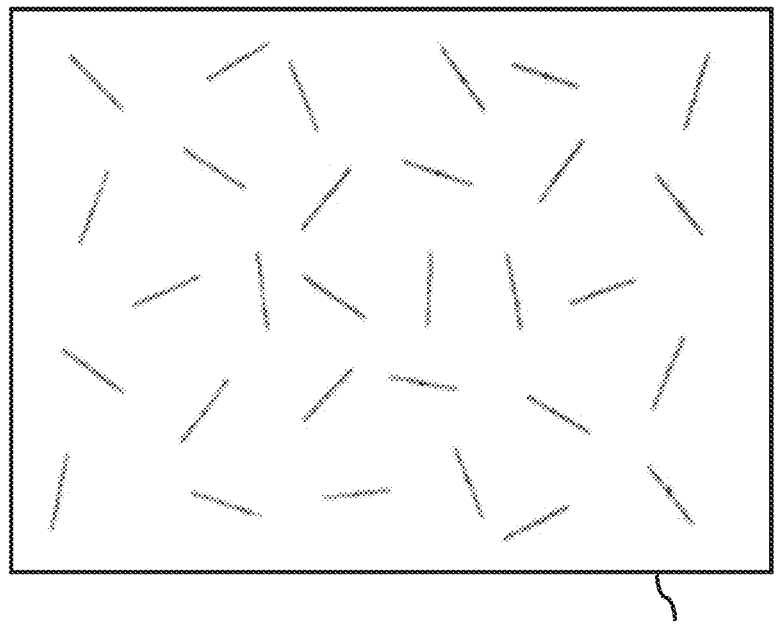
Fig. 2    200
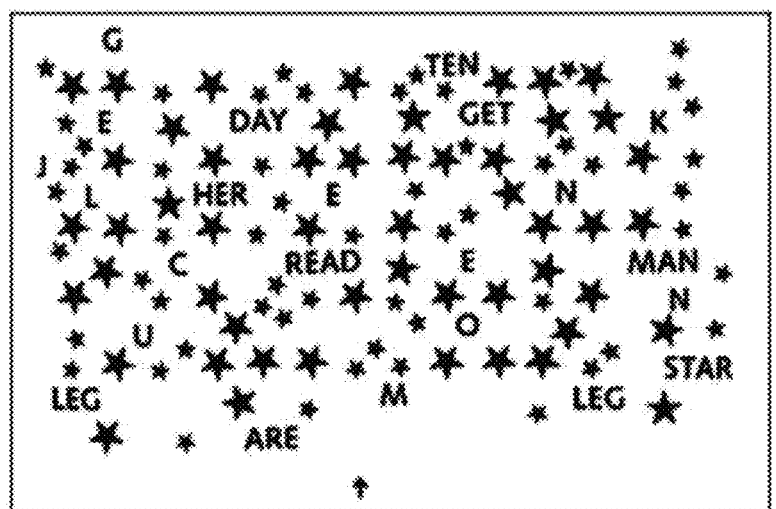
Fig. 3    210

ASSESSMENT OF AN ATTENTIONAL DEFICIT

CROSS-REFERENCE TO PRIOR APPLICATIONS

This application claims priority of European Application 14198284.3, filed Dec. 16, 2014. This application is incorporated by reference herein

FIELD OF THE INVENTION

The invention relates to a system and a method for use in an assessment of an attentional deficit. The invention further relates to a tablet device comprising the system and to a computer program product for causing a processor system to perform the method.

BACKGROUND OF THE INVENTION

A patient may have acquired brain damage from, e.g., a traumatic brain injury (TBI) or a stroke. After suffering TBI or a stroke, there are various cognitive tests that are performed for diagnosis and then monitoring of recovery of a patient. These tests are normally performed with paper and pencil, and the results are entered into the patient's record. However, there are several trends that establish a need for digitizing such tests. For example, digital tests are better suited to direct data storage and thereafter data mining to predict the (cognitive) recovery of the patient and help with rehabilitation planning. In addition, this information may potentially be used to stratify new TBI or stroke patients.

There is growing economic pressure to move TBI and stroke patients along the care continuum as fast as possible, resulting in more patients doing rehabilitation at home with a reduced amount of time with face to face therapist interaction. The inventors have recognized that this creates a need for digital cognitive tests that can be performed by the patient themselves in an unsupervised setting, thereby enabling the recovery of the patient to be monitored at a higher frequency and the therapy plan to be adjusted remotely, if needed.

A common symptom of TBI and stroke are attentional deficits, such as hemispatial neglect. The assessment of hemispatial neglect typically comprises the patient performing a task involving searching and crossing out specific stimuli, as shown in FIGS. 2 and 3. As with other types of cognitive tests used in the assessment of attentional deficits, the assessment of hemispatial neglect is typically performed in a paper/pencil format.

SUMMARY OF THE INVENTION

The inventors have recognized that a factor hindering automating the assessment of attentional deficits is the importance of a subject not moving his/her head with respect to the midline of a test image, and otherwise the test results will be void. As such, during a neuropsychological assessment, a neuropsychologist or other trained professional has to be present to observe the patient and to ensure he carries out the test as instructed. It would be advantageous to have a system or method for use in the assessment of an attentional deficit which avoids or reduces the need for a neuropsychologist or other trained professional to be present during the assessment.

A first aspect of the invention provides a system for use in an assessment of an attentional deficit, comprising:

a user interaction subsystem connectable to a display for presenting a test image to a subject as part of the assessment;

a camera for obtaining a camera image indicative of a geometric relation between the head of the subject and the display during the assessment;

an analysis subsystem for analyzing the camera image to determine a deviation in the geometric relation between the head of the subject and the display from a reference geometric relation; and a data interface for outputting deviation data indicative of the deviation to enable compensating for the deviation in the assessment.

A further aspect of the invention provides a tablet device comprising the system.

A further aspect of the invention provides a method for use in an assessment of an attentional deficit, comprising:

using a display, presenting a test image to a subject as part of the assessment;

obtaining a camera image indicative of a geometric relation between the head of the subject and the display during the assessment;

analyzing the camera image to determine a deviation in the geometric relation between the head of the subject and the display from a reference geometric relation; and outputting deviation data indicative of the deviation to enable compensating for the deviation in the assessment.

A further aspect of the invention provides a computer program product comprising instructions for causing a processor system to perform the method.

The above measures involve presenting a test image on a display to a subject as part of the assessment of the attentional deficit. Such a test image may take various forms, including but not limited to the test images shown in FIGS. 2 and 3. As such, the system may display a digital variant of a test image conventionally used in the paper/pencil tests.

A camera image is obtained which is indicative of a geometric relation between the head of the subject and the display during the assessment. Accordingly, the camera image may show part, or all, of the head of the subject and/or of the display. It may suffice, however, for the camera image to only show either of the two, e.g., if the geometric relation between the camera and a) the display and/or b) the subject is known. For example, the camera may be built into the display. Hence, it may suffice for the camera image to show (part of) the head of the subject, without showing the display. Conversely, the camera may be a wearable camera, e.g., as part of Google Glass or similar device. Hence, it may suffice for the camera image to show (part of) the display, without showing the subject itself.

The camera image is analyzed to determine a deviation in the geometric relation between the head of the subject and the display from a reference geometric relation. Here, the reference geometric relation may be presumed to be maintained by the subject during at least part of the assessment. For example, a valid assessment of attentional deficits such as hemispatial neglect may assume that the subject is positioned centrally with respect to the midline of the displayed test image. Accordingly, it may be determined from the camera image whether the subject is misaligned with respect to the midline of the displayed test image. It is noted that the geometric relation between the display and the displayed test image is known. The geometric relation between the displayed test image and the subject can thus be obtained by determining the geometric relation between the display and the subject.

The above measures have the effect that deviation data is obtained which is indicative of the deviation. This enables compensating for the deviation in the assessment of attentional deficits in various ways, e.g., still during the assessment or afterwards in evaluating the test data obtained from the assessment. The need for a neuropsychologist or other trained professional to be present during the assessment is thus avoided or reduced. Advantageously, a patient may complete the assessment in an unsupervised setting.

Optionally, the user interaction subsystem comprises a display processor for generating an output image for being presented on the display, the output image being generated based on the test image and the deviation data. By generating the output image based on the deviation data, the system is able to compensate for the deviation still during the test, for example, by providing visual feedback to the subject or by adjusting the test image.

Optionally, the display processor is configured for including a visual feedback element in the output image indicating whether the deviation is below or above a predetermined deviation threshold. It may be of relevance whether the deviation is below or above a predetermined deviation threshold. For example, a deviation within a predetermined range from the reference geometric relation may be deemed acceptable, whereas a deviation which exceeds said predetermined range may be deemed unacceptable. By providing a symbol, text or other type of visual feedback element in the output image, visual feedback is provided whether the deviation is below or above the predetermined deviation threshold. Advantageously, the subject is enabled to compensate for the deviation him/herself.

Optionally, the display processor is configured for generating the visual feedback element to be indicative of a direction in which the head of the subject is to be repositioned and/or reoriented so as to reduce the deviation. For example, the visual feedback element may be an arrow or other directional visual element. Advantageously, more specific visual feedback is provided to the subject, enabling faster and/or easier compensation.

Optionally, the display processor is configured for generating the visual feedback element in or as a border around the test image. A border around the test image is well suited for providing visual feedback since it avoids altering the test image itself. Moreover, a border may be easily perceivable while not being too distracting. For example, the border may be colored coded, providing a red border if the deviation is above the predetermined deviation threshold and a green border if the deviation is below said threshold.

Optionally, the display processor is configured for adjusting the test image as presented in the output image so as to account for the deviation in the geometric relation between the head of the subject and the display. Instead or in addition to providing visual feedback to the user, the test image may also be geometrically adjusted so as to compensate the deviation. For example, if the subject's head is rotated (roll) with respect to the display and the test image displayed thereon, the test image may be rotated so as to bring the test image in alignment with the subject's rotated head. Advantageously, it is not needed for the user to compensate for the deviation him/herself. Rather, the test image is suitably adjusted.

Optionally, the display processor is configured for adjusting the test image by rotating and/or translating the test image. Common forms of misalignment between the subject's head and the display involve mutual rotation and translation. Here, the term 'translation' refers to a misalignment with respect to a display plane of the display, e.g., when considering the position of the orthogonal projection of the subject's head onto the display plane. The display processor is thus enabled to compensate for such common misalignments.

Optionally, the user interaction subsystem is configured for recording test data representing user input obtained from the subject during the assessment, and the data interface is configured for storing the deviation data as metadata to the test data. Accordingly, the user interaction subsystem may record the subject's input during the assessment. Such input may involve positions on the display as selected by the subject, e.g., using a user input device. The deviation data is stored as metadata to the test data in that it may provide information about the test data, such as the geometric relation between the head of the subject and the display during the assessment. A non-limiting example is that the deviation data may indicate, for each on-screen position selected by the subject during the assessment, the current geometric relation between the head of the subject and the display. Advantageously, the deviation data may enable a more reliable analysis of the test data, in that it may allow, e.g., disregarding test results where the deviation in the geometric relation between the head of the subject and the display from the reference geometric relation is above a predetermined deviation threshold.

Optionally, the system further comprises an evaluation subsystem for processing the test data based on the deviation data to account for the deviation in the geometric relation between the head of the subject and the display in the test data. The evaluation subsystem may thus autonomously account for the deviation in the geometric relation between the head of the subject and the display from the reference geometric relation, e.g., by disregarding test results where the deviation exceeds a predetermined deviation threshold, or by compensating for said deviation in the analysis of the test data.

Optionally, the user interaction subsystem is configured for recording timing information as part of the test data, the timing information representing a reaction time of the subject during the assessment.

Optionally, the analysis subsystem is configured for analyzing the camera image to determine gaze points of the subject with respect to the display, and the user interaction subsystem is configured for recording gaze information as part of the test data. Optionally, the analysis subsystem is configured for applying a face recognition technique to the camera image to verify an identity of the subject participating in the assessment.

In accordance with the above, a system and method may be provided for use in the assessment of attentional deficits such as hemispatial neglect. During the assessment, a test image may be presented to a subject on a display. A camera image may be obtained from a camera which is indicative of a geometric relation between the head of the subject and the display during the assessment. The camera image may be analyzed to determine a deviation in the geometric relation between the head of the subject and the display from a reference geometric relation. Deviation data may then be generated and output which is indicative of the deviation. Advantageous uses of the deviation data include providing visual feedback to the user, adjusting the test image, and taking the deviation into account when processing test data of the assessment. Advantageously, the need for a trained professional to be present during the assessment may be reduced or avoided.

It will be appreciated by those skilled in the art that two or more of the above-mentioned embodiments, implementations, and/or optional aspects of the invention may be combined in any way deemed useful.

Modifications and variations of the tablet device, the method, and/or the computer program product, which correspond to the described modifications and variations of the system, can be carried out by a person skilled in the art on the basis of the present description.

The invention is defined in the independent claims. Advantageous embodiments are defined in the dependent claims.

BRIEF DESCRIPTION OF THE DRAWINGS

These and other aspects of the invention are apparent from and will be elucidated with reference to the embodiments described hereinafter. In the drawings.

FIGS. 2 and 3 show different known test images which may be used in the assessment of attentional deficits such as hemispatial neglect;

Figure 1:
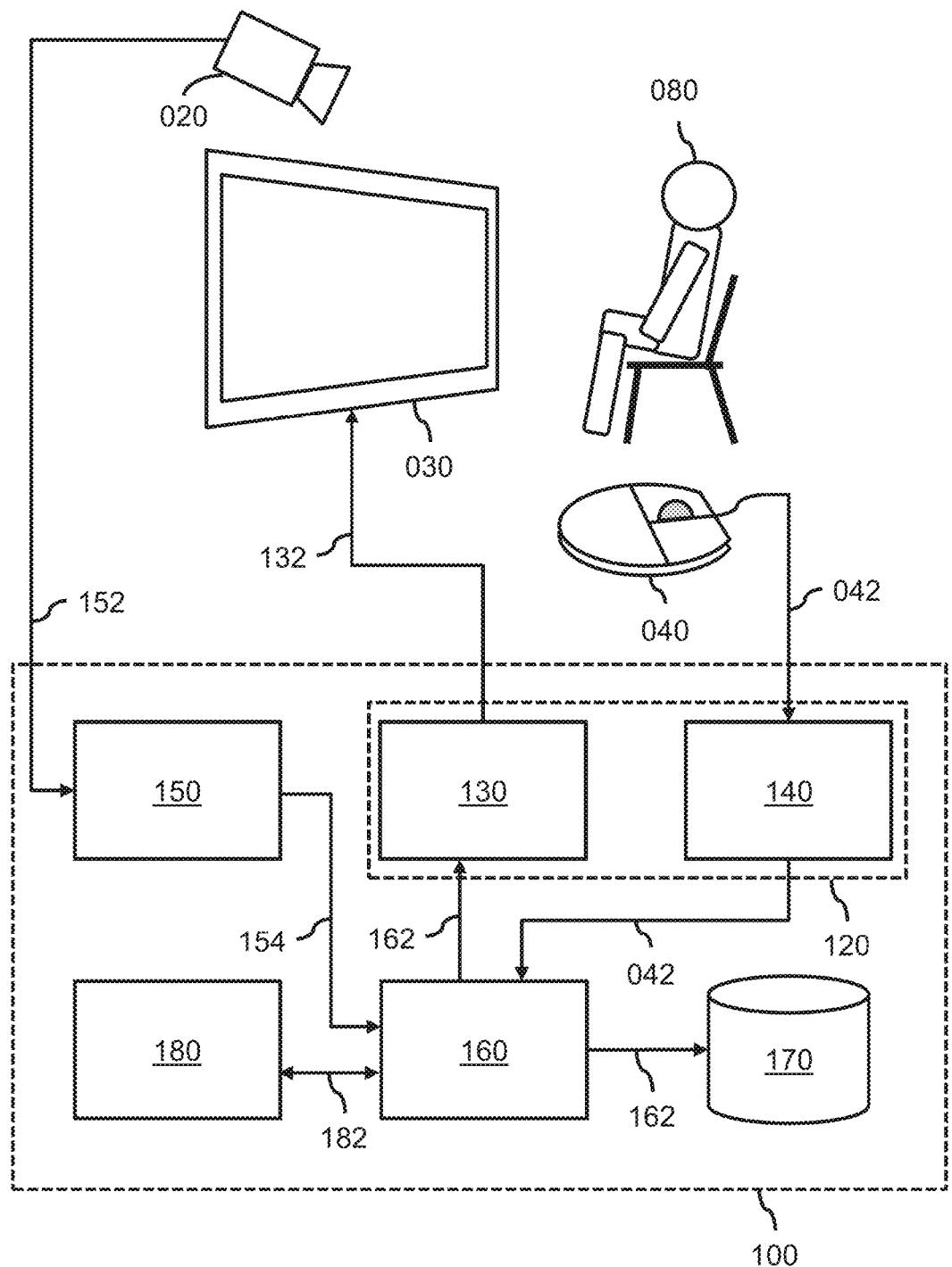
FIG. 1 shows a schematic overview of a system for use in the assessment of an attentional deficit, in which a test image is shown to a subject on a display.

It should be noted that items which have the same reference numbers in different Figures, have the same structural features and the same functions, or are the same signals. Where the function and/or structure of such an item have been explained, there is no necessity for repeated explanation thereof in the detailed description.

LIST OF REFERENCE NUMBERS

The following list of reference numbers is provided for facilitating the interpretation of the drawings and shall not be construed as limiting the claims.
020-022 camera
030-032 display
040 user input device
042 user input data
080 subject
100 system for use in assessment of an attentional deficit
110 tablet device comprising system
120 user interaction subsystem
130 display processor
132 display data
140 user input interface
150 analysis subsystem
152 camera image
154 communication to data interface
160 data interface
162 deviation data
170 data storage
180 evaluation subsystem
182 communication to/from evaluation subsystem
200-210 test image
202 test image adjusted by rotation
204 test image adjusted by translation
230 midline of displayed test image
300 reference geometric relation between head of subject and display
310 actual geometric relation between head of subject and display
400-408 output image
410 visual feedback element in form of border
412 visual feedback element in form of arrow
500 horizontal coordinate of selection point on display
502 rotation (roll) of head with respect to display
510 selection points in case of no hemispatial neglect, no head rotation
512 selection points in case of hemispatial neglect, no head rotation
514 selection points in case of no hemispatial neglect, head rotation
516 selection points in case of hemispatial neglect, head rotation
600 method for use in assessment of an attentional deficit
610 displaying test image
620 obtaining camera image
630 determining deviation in geometric relation
640 outputting deviation data
650 computer readable medium
660 non-transitory data representing instructions

DETAILED DESCRIPTION OF EMBODIMENTS

FIG. 1 shows a schematic overview of a system 100 for use in the assessment of an attentional deficit. The system 100 comprises a user interaction subsystem 120 which is shown to be connected to a display 030, thereby enabling the user interaction subsystem 120 to present a test image to a subject 080 as part of the assessment. In the example of FIG. 1, the user interaction subsystem 120 is shown to comprise a display processor 130 which provides display data 132 to the display 030, with the display data 132 representing an output image which comprises, or is constituted by, the test image. Moreover, the user interaction subsystem 120 is shown to comprise a user input interface 140 for receiving user input data 042 from a user input device 040 operated by the subject, such as a mouse, keyboard, touch screen, etc. Accordingly, the user interaction subsystem 120 may record test data representing user input obtained from the subject 080 during the assessment. It will be appreciated that the user interaction subsystem 120 may also take any other form which is suitable for presenting a test image to the subject.

The system 100 further comprises a camera 020 for obtaining a camera image 152 which is indicative of a geometric relation between the head of the subject 080 and the display 030 during the assessment. The system 100 further comprises an analysis subsystem 150 for analyzing the camera image 152 to determine a deviation in the geometric relation between the head of the subject and the display from a reference geometric relation. Here, the reference geometric relation may be a geometric relation which is presumed to be maintained by the subject during at least part of the assessment. For example, the reference geometric relation may denote the subject's head being aligned with a midline of the test image.

The system 100 further comprises a data interface 160 for outputting deviation data 162 indicative of the deviation to enable compensating for the deviation in the assessment of attentional deficits such as hemispatial neglect. In the example of FIG. 1, the deviation data 162 is shown to be provided to the display processor 130 and stored in a data storage 170. The data storage 170 is shown to be an internal component of the system 100, and may be constituted by, e.g., a disk-based data storage such as a hard disk, a semiconductor-based data storage such as a ROM or RAM memory, a removable storage medium inserted into a storage medium reader, etc. It is noted that the data storage 170 may also be externally provided, e.g., in the form of a removable storage medium or as a network attached data storage. In general, the data interface 160 may take various forms, such as a network interface to a local or wide area network, such as the Internet, a storage interface to an internal or external data storage, etc.

FIG. 1 shows a further optional aspect of the system 100, in that the system 100 may comprise an evaluation subsystem 180 for processing the test data recorded by the user interaction subsystem 120. This aspect will be further explained in reference to FIGS. 9A-9D.

In general, the operation of the system of FIG. 1, including various optional aspects thereof, will be explained in more detail in reference to FIGS. 2-9.

It is noted that the system 100 may be embodied as, or in, a single device or apparatus, such as a tablet device, smartphone, etc. The device or apparatus may comprise one or more microprocessors which execute appropriate software. The software may have been downloaded and/or stored in a corresponding memory, e.g., a volatile memory such as RAM or a non-volatile memory such as Flash. Alternatively, the functional units of the system may be implemented in the device or apparatus in the form of programmable logic, e.g., as a Field-Programmable Gate Array (FPGA). In general, each functional unit of the system may be implemented in the form of a circuit. It is noted that the system 100 may also be implemented in a distributed manner, e.g., involving different devices or apparatuses.

FIGS. 2 and 3 show different known test images 200-210 which may be used in the assessment of hemispatial neglect. FIG. 2 shows a so-termed line crossing test image 200 in which the subject is requested to cross out all lines. When displaying the test image 200 digitally, i.e., on the display, the subject may cross out the lines by providing appropriate user input, e.g., by selecting a line with a mouse cursor or by touching the line on a touch-equipped display. FIG. 3 shows a so-termed star cancellation test image 210 as developed by Wilson, Cockburn, and Halligan. Here, the subject is requested to cross out all the small stars. The system 100 of FIG. 1 may make use of test images such as those of FIGS. 2 and 3. However, this is not a limitation, in that any other test image suitable for the assessment of attentional deficits may be used as well by the system 100 of FIG. 1. In particular, the attentional deficit may not need to be associated with hemispatial neglect, but rather be of a type where, in the assessment of the attentional deficit, the geometric relation between the subject and the displayed test image during the assessment is of relevance for the validity of the test results.

Figure 4:
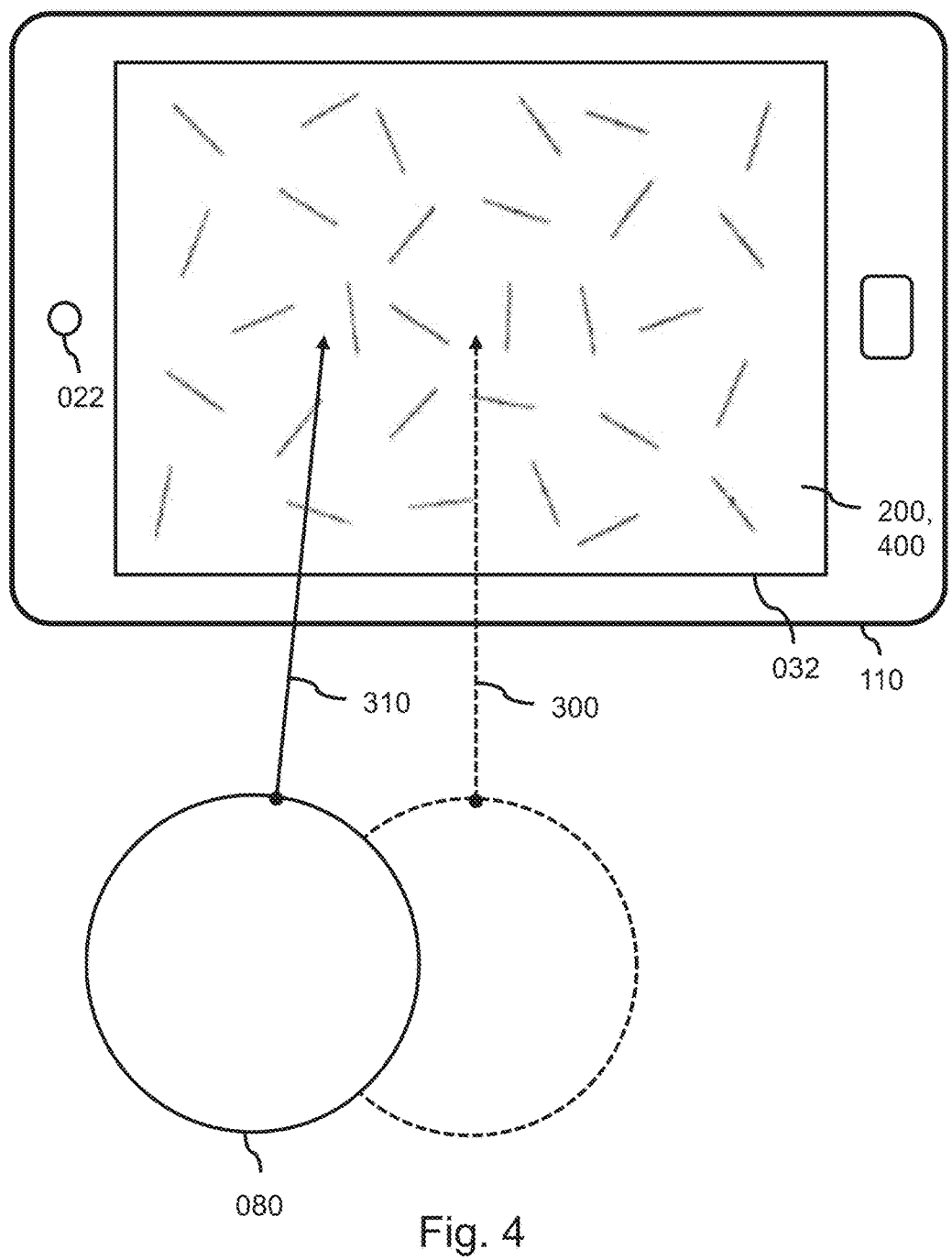
FIG. 4 shows a tablet device comprising the system, while further illustrating the geometric relation between the head of the subject and the display.

FIG. 4 shows a system for use in the assessment of an attentional deficit having been integrated into a tablet device 110. As such, use may be made of the front-facing camera 022 and the display 032 of the tablet device 110. Namely, a test image 200 may be displayed as part of an output image 400 on the tablet's display 032 while the tablet's camera 022 records a camera image showing the subject's head 080 when viewing the test image 200. From the camera image, it may be determined that a misalignment exists between the head of the subject 080 and the displayed test image 200, or in general, any other form of deviation of the head of the subject from a reference position and/or orientation relative to the display 032. In FIG. 4, the relative position and/or orientation which is presumed to be maintained by the subject 080 during (part of) the assessment is shown by a dashed arrow 300 originating from a dashed outline of the head, representing a reference geometric relation between the head 080 and the display 032. As can be seen from FIG. 4, the actual geometric relation 310 between the head of the subject 080 and the display 032 may deviate from the reference geometric relation 300. In the example of FIG. 4, this deviation is predominately a deviation in relative position, and to a lesser degree, a deviation in relative orientation. Although not shown explicitly in FIG. 4, a deviation in relative orientation may involve a relative rotation of the subject's head, e.g., involving a relative roll, yaw or pitch.

In order to detect the position and/or orientation of the head of the subject in the camera image, various techniques may be used including face detection, pose estimation, etc. It is noted that detecting the position of the head in a camera image is typically less challenging and thus more reliable than detecting the orientation of the face/head. Nevertheless, various techniques are known within the field of computer vision which provide sufficient reliability in detecting the orientation of the head in a camera image. Such techniques are also referred to as head pose estimation, providing roll, yaw and pitch angles.

Figure 5:
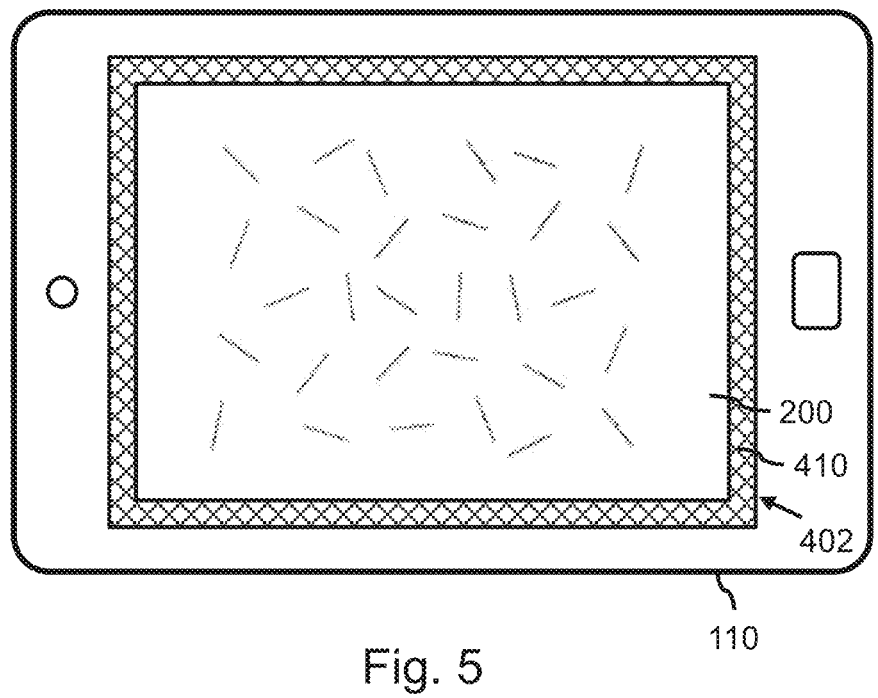
FIG. 5 shows an example of an output image in which a visual feedback element is included in the form of a colored border surrounding the test image.
Figure 6:
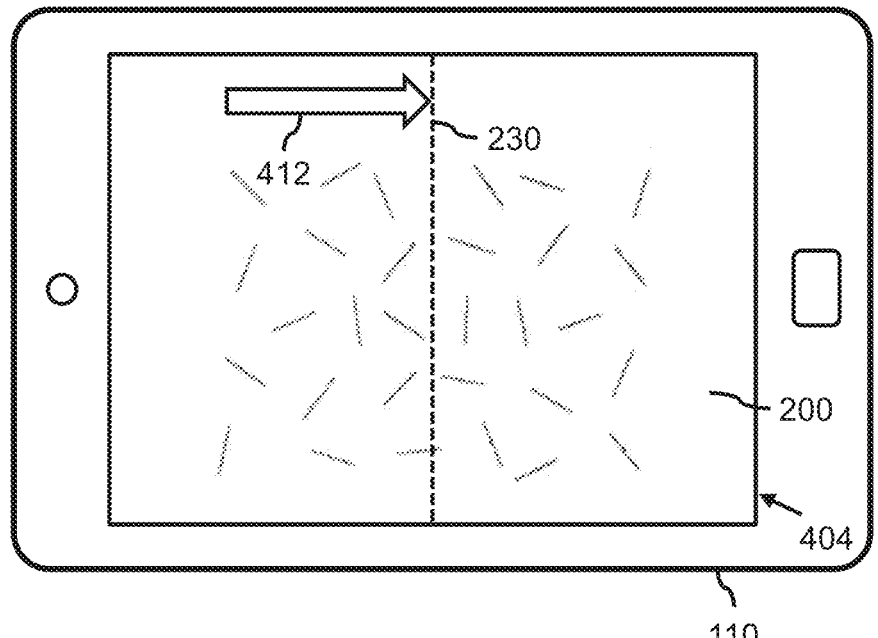
FIG. 6 shows another example of an output image in which another type of visual feedback element is included, namely a directional indicator.

FIGS. 5 and 6 relate to the following use of the deviation data generated by the system. Namely, a visual feedback element may be included in the output image indicating whether the deviation is below or above a predetermined deviation threshold.

FIG. 5 shows an example of an output image 402 in which a visual feedback element is included in the form of a colored border 410 surrounding the test image. For example, the border 410 may be displayed in red when the deviation is above a predetermined deviation threshold, and in green when the deviation is below the predetermined deviation threshold. In a specific example, the border 410 may be green when pose of the head is detected and the rotation (roll) of the head is found to be within 10 degrees of the horizontal plane of the display. Otherwise, the border 410 may be displayed in red. The subject may be instructed to only perform the test when the border is green.

FIG. 6 shows another example of an output image 404 in which another type of visual feedback element is included, namely a directional indicator in the form of an arrow 412. The directional indicator is an example of a visual feedback element which may be generated to be indicative of a direction in which the head of the subject is to be repositioned and/or reoriented so as to reduce the deviation. In the example of FIG. 6, the arrow 412 may indicate that the subject should move the head towards the right relative to the tablet device so as to reduce the deviation. The directional indicator may also indicate a magnitude of the deviation. For example, the length of the arrow 412 may be shortened when the deviation is reduced by the subject appropriately moving his/her head, and may disappear when the subject assumes the desired position above the midline 230 of the displayed test image.

Figure 7:
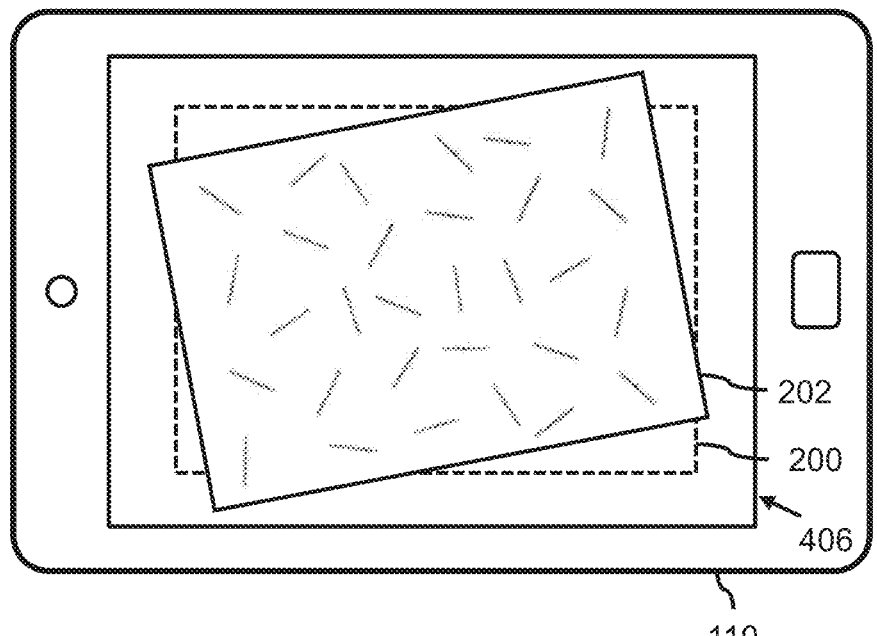
FIG. 7 shows another example of an output image in which the test image is rotated to account for a rotation of the subject's head with respect to the display.
Figure 8:
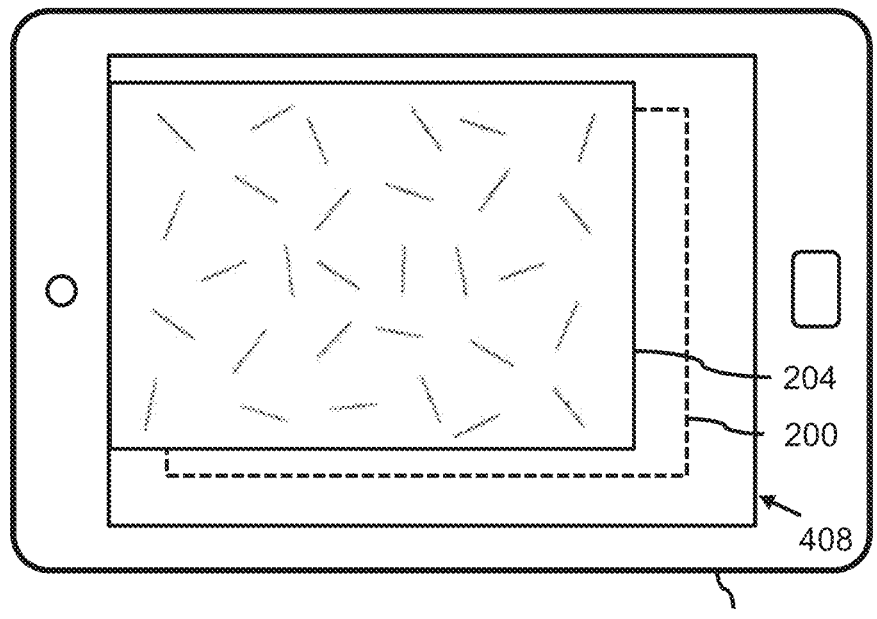
FIG. 8 shows another example of an output image in which the test image is translated to account for a misalignment of the subject's head with respect to the display.

FIGS. 7 and 8 relate to another use of the deviation data generated by the system. Namely, the test image as presented in the output image may be adjusted so as to account for the deviation in the geometric relation between the head of the subject and the display. Such adjustment may take various forms, such as rotation and translation. The former is shown in FIG. 7, in which the output image 406 comprises a rotated test image 202 so as to compensate for a rotation (roll) of the subject's head with respect to the display, whereas the latter is shown in FIG. 8, in which the output image 408 comprises translated test image 204. In both Figs., the non-rotated, non-translated test image is shown as a dashed outline 200. It is noted that various other forms of adjustment are equally conceivable. For example, an affine transformation may be applied to the test image which provides a rendering of the test image on the display that appears centrally within the field of view of the subject when viewed from the subject at his/her relative position and/or orientation.

FIGS. 9A-9D relate to yet another use of the deviation data generated by the system. Here, as example of an attentional deficit, the one-sided reduced visual awareness associated with hemispatial neglect is chosen, also referred to in the following in-short as 'assessment of hemispatial neglect'. When recording test data representing user input obtained from the subject during the assessment of hemispatial neglect, the deviation data may be stored as metadata to the test data. This may enable accounting for the deviation in the geometric relation between the head of the subject and the display in the processing of the test data, e.g., in further automatic processing by an evaluation subsystem or in further manual processing. For example, and as also illustrated in FIGS. 9A-9D, the deviation may be set out against the horizontal coordinate of a user's selection on the display. Namely, in FIGS. 9A-9D, the vertical axis 502 represents a rotation (roll) of the subject's head with respect to the display within a range of [180, 0] degrees, with 0 degrees corresponding to eye plane of the user (defined as a plane running through both eyes of the user extending perpendicular from the face) being aligned with a horizontal axis of the display, and other values representing a mutual rotation (roll) with respect to that alignment. The horizontal axis 500 represents the horizontal coordinate of a selection point on the display. Selections points indicated by 'X' thus represent a particular user input, e.g., a selection (e.g., crossing) of an object (e.g., line, star) on the display by the user, in which its horizontal coordinate is set out against the current angle of rotation (roll) of the subject's head with respect to the display.

Figures 9A, 9B:
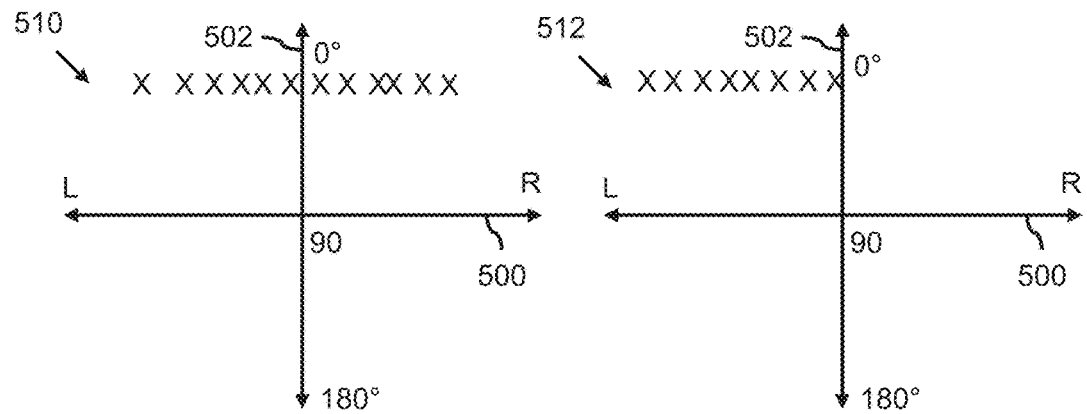
FIGS. 9A-D illustrate deviation data being used in the processing of test data representing user input obtained from the subject during the assessment.
Figures 9C, 9D:
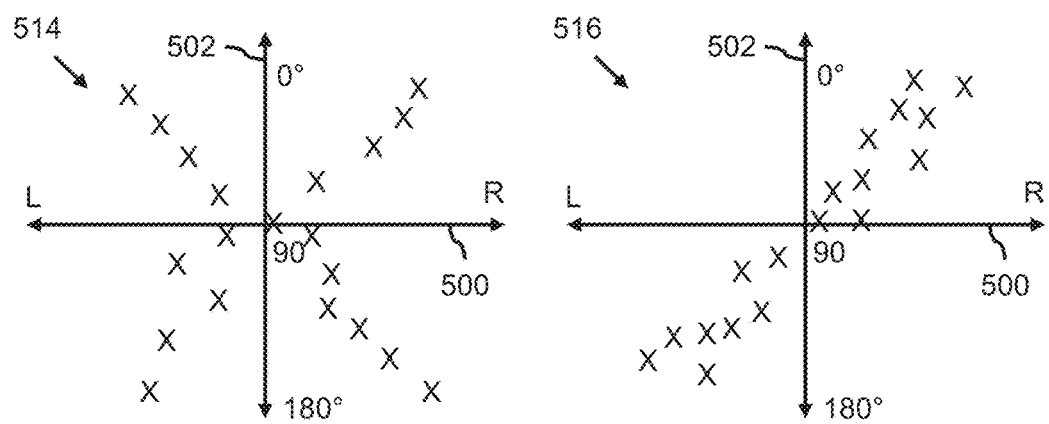

The thus obtained graph(s) may then be analyzed to determine in which part of the visual field of the subject the object was present when selected. It can be seen from FIGS. 9A-9D that distinctive patterns emerge depending on whether or not the subject suffered from hemispatial neglect, and whether or not the subject rotated his/her head during the assessment. Namely, there are two possible reasons that the subject can see all the targets in both sides of the display: he/she has no hemispatial neglect or that the display is rotated with respect to the head and therefore the contents of the two sides of the displayed test image are not aligned with the visual fields. Measuring the rotation angle allows separating these from one another. In other words, if the geometric relation between the head of the subject and the display is known, it can be determined whether a crossed target was in the left or right visual field of the subject when identified by the subject. Here, FIG. 9A shows selection points 510 in case of no hemispatial neglect and no head rotation, and FIG. 9B shows selection points 512 in case of hemispatial neglect and no head rotation. FIG. 9C shows selection points 514 in case of no hemispatial neglect and head rotation. Here, there is various rotation during the assessment but the targets 514 are evenly distributed over the four quadrants, i.e., recognized in the left and right sides of the displayed test image irrespective of the rotation angle. As such, it may be concluded that there is no hemispatial neglect. However, in FIG. 9D, there appears to be hemispatial neglect as the targets 516 are only crossed when rotated into the non-affected field. It is noted that if the rotation angle was not known, then FIG. 9D would be a linear projection and would give a false result of there not being hemispatial neglect.

The inventors have further recognized that a digital neuropsychological assessment opens the possibility for the measurement of additional behavioral aspects and parameters, such as eye movement, search patterns and reaction time. In particular, the device(s) on which the tests are presented, such as a tablet device, may be used to monitor the patient's behavior during completion of the test and if necessary to correct the test score accordingly. This may be of particular relevance when tests are conducted in an uncontrolled environment, such as is the case for TBI or stroke out-patients who are participating in rehabilitation programs. In accordance with the above, timing information may be recorded as part of the test data, the timing information representing a reaction time of the subject during the assessment. Additionally or alternatively, the camera image may be analyzed to determine gaze points of the subject with respect to the display, and the gaze information may be recorded as part of the test data. It is noted that techniques for determining gaze points of a subject from a camera image of the subject are known per se and may be advantageously used to determine the gaze points from the camera image. Additionally or alternatively, a face recognition technique may be applied to the camera image to verify an identity of the subject participating in the assessment. As such, it may be verified whether or not the subject shown in the camera image corresponds to the subject in which attentional deficits are to be assessed.

Figure 10:
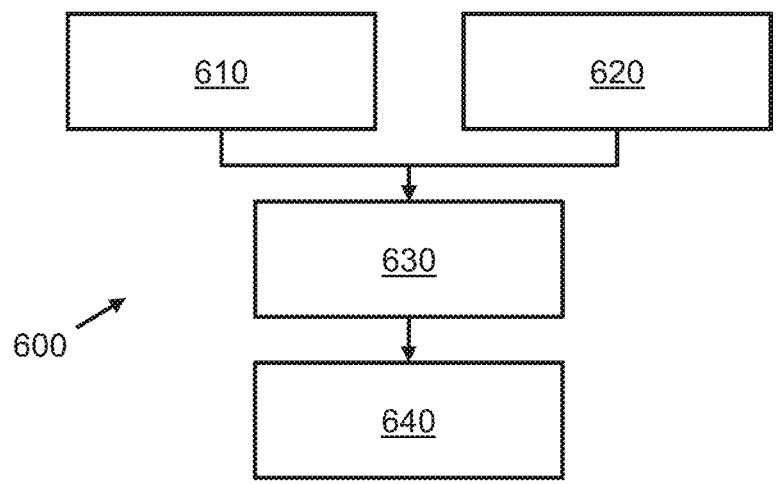
FIG. 10 shows a method for use in the assessment of an attentional deficit.

FIG. 10 shows a method 600 for use in the assessment of an attentional deficit. The method 600 may correspond to an operation of the system 100 of FIG. 1. However, this is not a limitation, in that the method 600 may also be performed using one or more different devices or apparatuses. The method 600 comprises, in an operation titled "DISPLAYING TEST IMAGE", presenting 610, using a display, a test image to a subject as part of the assessment. The method 600 further comprises, in an operation titled "OBTAINING CAMERA IMAGE", obtaining 620 a camera image indicative of a geometric relation between the head of the subject and the display during the assessment. The method 600 further comprises, in an operation titled "DETERMINING DEVIATION IN GEOMETRIC RELATION", analyzing 630 the camera image to determine a deviation in the geometric relation between the head of the subject and the display from a reference geometric relation. The method 600 further comprises, in an operation titled "OUTPUTTING DEVIATION DATA", outputting 640 deviation data indicative of the deviation to enable compensating for the deviation in the assessment.

It will be appreciated that the above operation may be performed in any suitable order, e.g., consecutively, simultaneously, or a combination thereof, subject to, where applicable, a particular order being necessitated, e.g., by input/output relations.

Figure 11:
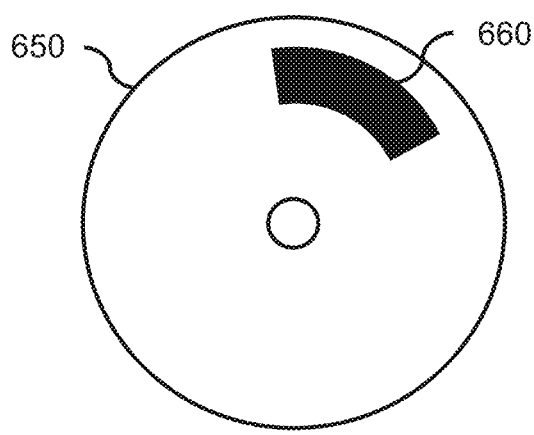
FIG. 11 shows a computer readable medium comprising instructions for causing a processor system to perform the method.

The method 600 may be implemented on a computer as a computer implemented method, as dedicated hardware, or as a combination of both. As also illustrated in FIG. 11, instructions for the computer, e.g., executable code, may be stored on a computer readable medium 650, e.g., in the form of a series 660 of machine readable physical marks and/or as a series of elements having different electrical, e.g., magnetic, or optical properties or values. The executable code may be stored in a transitory or non-transitory manner. Examples of computer readable mediums include memory devices, optical storage devices, integrated circuits, servers, online software, etc. FIG. 11 shows an optical disc 650.

It will be appreciated that the invention also applies to computer programs, particularly computer programs on or in a carrier, adapted to put the invention into practice. The program may be in the form of a source code, an object code, a code intermediate source and an object code such as in a partially compiled form, or in any other form suitable for use in the implementation of the method according to the invention. It will also be appreciated that such a program may have many different architectural designs. For example, a program code implementing the functionality of the method or system according to the invention may be sub-divided into one or more sub-routines. Many different ways of distributing the functionality among these sub-routines will be apparent to the skilled person. The sub-routines may be stored together in one executable file to form a self-contained program. Such an executable file may comprise computer-executable instructions, for example, processor instructions and/or interpreter instructions (e.g. Java interpreter instructions). Alternatively, one or more or all of the sub-routines may be stored in at least one external library file and linked with a main program either statically or dynamically, e.g. at run-time. The main program contains at least one call to at least one of the sub-routines. The sub-routines may also comprise function calls to each other. An embodiment relating to a computer program product comprises computer-executable instructions corresponding to each processing stage of at least one of the methods set forth herein. These instructions may be sub-divided into sub-routines and/or stored in one or more files that may be linked statically or dynamically. Another embodiment relating to a computer program product comprises computer-executable instructions corresponding to each means of at least one of the systems and/or products set forth herein. These instructions may be sub-divided into sub-routines and/or stored in one or more files that may be linked statically or dynamically.

The carrier of a computer program may be any entity or device capable of carrying the program. For example, the carrier may include a data storage, such as a ROM, for example, a CD ROM or a semiconductor ROM, or a magnetic recording medium, for example, a hard disk. Furthermore, the carrier may be a transmissible carrier such as an electric or optical signal, which may be conveyed via electric or optical cable or by radio or other means. When the program is embodied in such a signal, the carrier may be constituted by such a cable or other device or means. Alternatively, the carrier may be an integrated circuit in which the program is embedded, the integrated circuit being adapted to perform, or used in the performance of, the relevant method.

It should be noted that the above-mentioned embodiments illustrate rather than limit the invention, and that those skilled in the art will be able to design many alternative embodiments without departing from the scope of the appended claims. In the claims, any reference signs placed between parentheses shall not be construed as limiting the claim. Use of the verb "comprise" and its conjugations does not exclude the presence of elements or stages other than those stated in a claim. The article "a" or "an" preceding an element does not exclude the presence of a plurality of such elements. The invention may be implemented by means of hardware comprising several distinct elements, and by means of a suitably programmed computer. In the device claim enumerating several means, several of these means may be embodied by one and the same item of hardware. The mere fact that certain measures are recited in mutually different dependent claims does not indicate that a combination of these measures cannot be used to advantage.

The invention claimed is:

1. A system for use in an assessment of an attentional deficit, comprising:
   a display;
   a camera configured to obtain a camera image indicative of a geometric relation between a head of a subject and the display during an assessment; and
   one or more processors configured by machine-readable instructions to:
   effectuate presentation of a test image on the display to the subject as part of the assessment;
   determine, based on the camera image, a deviation in the geometric relation between the head of the subject and the display from a reference geometric relation, wherein the reference geometric relation is determined based on a marker included in the test image;
   determine, based on the camera image, gaze points of the subject with respect to the display; and
   determine attentional deficit of the subject based on the determined deviation and the determined gaze points.

2. The system according to claim 1, wherein the one or more processors are further configured to effectuate presentation of an output image based on the test image and the deviation data.

3. The system according to claim 2, wherein the one or more processors are further configured to provide a visual feedback element in the output image indicating whether the deviation is below or above a predetermined deviation threshold.

4. The system according to claim 3, wherein the one or more processors are configured to generate the visual feedback element to be indicative of a direction in which the head of the subject is to be repositioned and/or reoriented so as to reduce the deviation.

5. The system according to claim 3, wherein the one or more processors are configured to generate the visual feedback element in or as a border around the test image.

6. The system according to claim 2, wherein the one or more processors are configured to adjust the test image based on the deviation in the geometric relation between the head of the subject and the display.

7. The system according to claim 6, wherein the one or more processors are configured such that adjusting the test image comprises rotating and/or translating the test image.

8. The system according to claim 1, wherein the one or more processors are further configured to:
   record test data representing (i) user input obtained from the subject during the assessment and (ii) the gaze points, and store the deviation data as metadata to the test data.

9. The system according to claim 8, wherein the one or more processors are further configured to disregard test data responsive to the deviation exceeding a predetermined deviation threshold.

10. The system according to claim 8, wherein the one or more processors are further configured to record timing information as part of the test data, the timing information representing a reaction time of the subject during the assessment.

11. The system according to claim 5, wherein the one or more processors are configured such that the border comprises (i) a first color responsive to the deviation being below the predetermined deviation threshold and (ii) a second color responsive to the deviation being above the predetermined deviation threshold, wherein the second color is different from the first color.

12. The system according to claim 1, wherein the one or more processors are configured to verify, via facial recognition applied to the camera image, an identity of the subject participating in the assessment.

13. The system according to claim 7, wherein the one or more processors are configured such that adjusting the test image comprises rotating the test image and wherein rotating the image comprises turning the test image around a point within the test image and/or axis corresponding to the test image.

14. A method for assessing an attentional deficit of a subject with a system, the system including a camera, a display, and one or more processors, the method comprising:
   effectuating, with the one or more processors, presentation of a test image on the display to the subject as part of the assessment;
   determining, with the one or more processors and based on a camera image obtained from the camera, a deviation in the geometric relation between the head of the subject and the display from a reference geometric relation, wherein the reference geometric relation is determined based on a marker included in the test image;
   determining, with the one or more processors and based on the camera image, gaze points of the subject with respect to the display; and
   determining, with the one or more processors, attentional deficit of the subject based on the determined deviation and the determined gaze points.

15. The system according to claim 1, wherein the test image comprises one or more objects for selection based on user input obtained from the subject during the assessment and wherein the one or more processors are configured to (i) determine a position of one or more selected objects in the subject's visual field and (ii) determine hemispatial neglect based on a pattern emerged from the position of the one or more selected objects in the subject's visual field.

16. A system configured to assess an attentional deficit, the system comprising:
   a display;
   a camera configured to obtain a camera image indicative of a geometric relation between a head of a subject and the display during an assessment; and
   one or more processors configured by machine-readable instructions to:
      effectuate presentation of a test image on the display to the subject as part of the assessment;
      determine, based on the camera image, a deviation in the geometric relation between the head of the subject and the display from a reference geometric relation, wherein the reference geometric relation is determined based on a marker included in the test image; and
      determine hemispatial neglect of the subject based on the determined deviation.

17. The system according to claim 1, wherein the reference geometric relation corresponds to an alignment of the head of the subject with respect to the marker displayed on the test image, wherein the marker is a vertical line included in the image.

* * * * *